United States Patent [19]

Pigerol et al.

[11] 4,264,773

[45] Apr. 28, 1981

[54] PREPARATION OF 2-CHLORO-THIOXANTHONE

[75] Inventors: Charles Pigerol, Saint-Ouen; Michel Bouisset; Michel Chignac, both of Sisteron; Claude Grain, Volonne, all of France

[73] Assignee: Labaz, Paris, France

[21] Appl. No.: 17,830

[22] Filed: Mar. 5, 1979

[30] Foreign Application Priority Data

Mar. 9, 1978 [FR] France ................. 78 06741

[51] Int. Cl.$^3$ .................. C07D 335/16; C07C 121/60
[52] U.S. Cl. ................. 549/27; 260/465 G; 562/432
[58] Field of Search ............ 260/465 G, 328; 549/27

[56] References Cited

U.S. PATENT DOCUMENTS 3,711,513  1/1973  Schulenberg ................. 260/328

FOREIGN PATENT DOCUMENTS 1173489  10/1958  France .

OTHER PUBLICATIONS

Leandri et al., Chemical Abstracts, vol. 52, 7291-7292, (1958).
Watanabe et al., Chemical Abstracts, vol. 73, 55813c, (1970).

Primary Examiner—Dolph H. Torrence
Attorney, Agent, or Firm—Mason, Kolehmainen, Rathburn & Wyss

[57] ABSTRACT

The invention relates to 2-(4'-chloro-phenylthio)-benzonitrile, to its process of preparation and to its use for preparing 2-chlorothioxanthone.

2-Chloro-thioxanthone prepared from the compound of the invention is useful as a photoinitiator for the reticulation of synthetic resins and as an intermediate for preparing pharmaceuticals.

1 Claim, No Drawings

PREPARATION OF 2-CHLORO-THIOXANTHONE

The present invention relates to a new derivative of benzonitrile useful as starting-product for preparing 2-chloro-thioxanthone.

The invention relates more particularly to 2-(4'-chloro-phenylthio)-benzonitrile of the formula:

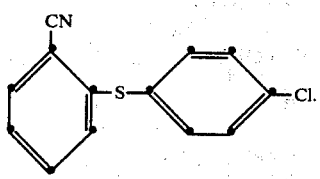

The invention also relates to the process of preparation of the compound of formula I, whereby an alkali metal derivative of 4-chloro-thiophenol is reacted in an organic solvent with 2-chloro-benzonitrile.

Finally, the invention relates to the use of the compound of formula I for preparing 2-chloro-thioxanthone, whereby 2-(4'-chloro-phenylthio)-benzonitrile is hydrolysed in an acid or basic medium, to give 2-(4'-chloro-phenylthio)-benzoic acid which is cyclized by dehydration to give 2-chloro-thioxanthone.

2-(4'-Chloro-phenylthio)-benzonitrile is a new compound and is claimed as such. It enables 2-chloro-thioxanthone to be obtained by a new and advantageous method. This latter product is known as a photoinitiator for the reticulation of synthetic resins, namely acrylic resins, as described in U.S. Pat. No. 3,876,519. It is also known as an intermediate for preparing pharmaceuticals, as described in French Pat. No. 1,352,102.

French Pat. No. 1,173,489 discloses a process for preparing 2-chloro-thioxanthone whereby an alkali metal derivative of 4-chloro-thiophenol is reacted with a 2-halogeno benzoic acid to give 2-(4'-chloro-phenylthio)-benzoic acid which is cyclized by dehydration to give 2-chloro-thioxanthone.

This process differs from the process of the invention in that the 2-halogeno-benzoic acid is used as starting-product for preparing the 2-(4'-chloro-phenylthio)-benzoic acid, without using the 2-(4'-chloro-phenylthio)-benzonitrile, the compound of the invention.

This process, which would appear to be more direct, could not however, be used on an industrial scale for not only does it give low yields, but it also involves the use of expensive starting-products.

For instance, the reaction of an alkali metal derivative of 4-chloro-thiophenol with 2-chloro-benzoic acid gives 2-(4'-chloro-phenylthio)-benzoic acid in a yield which does not exceed 20 to 30%. This is too low a yield to enable an industrial application of this reaction to be considered.

With regard to the reaction with 2-bromo-benzoic acid, this gives a better yield, which may reach 50%, but this figure is still too low to compensate for the higher cost of this reactant. Finally, the reaction with 2-iodo-benzoic acid gives a yield of about 40 to 50%, which is too low a yield for profitable use on the industrial scale. Moreover, 2-iodo-benzoic acid is fairly expensive and not easy to find on the market.

As against this, the reaction involving the use of 2-(4'-chloro-phenylthio)-benzonitrile, the compound of the invention, enables 2-chloro-thioxanthone to be obtained with excellent yields, in the region of 80 to 85%, and from starting-products which are both cheap and readily available on the market.

There is also known a process for preparing a compound similar to 2-chloro-thioxanthone, namely 1-chloro-thioxanthone, a starting-product for preparing hycanthone.

U.S. Pat. No. 3,711,513 teaches the preparation of 1-chloro-thioxanthone by reacting 2,6-dichloro-benzonitrile with an alkali metal salt of thiophenol to obtain 2-chloro-6-phenylthio-benzonitrile, which is reacted with polyphosphoric acid to give 1-chloro-9-imino-thioxanthene, this latter product being hydrolysed to 1-chloro-thioxanthone.

Apart from the reactants and the final product, this process is different from that of the invention in that the 2-chloro-6-phenylthio-benzonitrile is not hydrolysed but directly cyclized to 1-chloro-9-imino thioxanthene. It is this latter product which is hydrolysed to give 1-chloro-thioxanthone.

This difference is important and it should be emphasized that the above described process is most unprofitable and could not be used on an industrial scale: its total yield in 1-chloro-thioxanthone does not in fact reach 15%.

The following Examples illustrate in a non-limitative manner the process of preparation of the compound of the invention and the use of this compound for preparing 2-chloro-thioxanthone.

EXAMPLE 1

Preparation of 2-(4'-chloro-phenylthio)-benzonitrile

Into a 2-liter glass reactor fitted with a condenser, a stirrer, a dropping funnel and a source of nitrogen were introduced 200 g of methanol and 23 g (1 at.g.) of sodium were added slowly. As soon as the sodium had reacted, 80 g of methanol were distilled off.

The reaction medium was cooled and 144.5 g (1 mol) of 4-chlorothiophenol were added in one operation.

The mixture was refluxed for 15 minutes and was cooled to 80° C. after which a solution of 133.5 g (0.97 mol) of 2-chloro-benzonitrile in 300 g of toluene was rapidly added, followed by 94.5 g of N,N-dimethylformamide whereupon 250 g of the azeotrope toluene-methanol were distilled off and then 80 g of toluene. The reaction medium was heated to 125°-130° C. for 1.5 hour and was cooled to 60° C. and then 420 g of toluene and 200 g of water were added.

The mixture was decanted at 50° C. and the organic phase was washed with 200 g of a 5% aqueous solution of sodium hydroxide, then twice with 200 g of the same solution, the temperature being maintained at 50° C.

The toluene was eliminated and 226.44 g of 2-(4'-chloro-phenylthio)-benzonitrile were obtained, corresponding to a yield of 95% in crude product.

The crude substance melts at 82° C. and, after recrystallization from ethanol, at 87° C.

It is not, in fact, necessary to isolate the 2-(4'-chlorophenylthio)-2 benzonitrile as the toluene solution of this product can be used per se for preparing 2-(4'-chloro-phenylthio)-benzoic acid, which is subsequently transformed into 2-chloro-thioxanthone.

EXAMPLE 2

Preparation of 2-(4'-chloro-phenylthio)-benzonitrile

Into a 250 ml-reactor fitted with a Dean-Stark apparatus and a source of nitrogen were introduced 28.9 g (0.2 mol) of 4-chloro-thiophenol and a solution of 8.2 g (0.205 mol) of sodium hydroxide in 30 g of water.

The temperature of the mixture rose to 50°–60° C. and this temperature was maintained for 30 minutes after which 30 ml of benzene were added. About half of the water was eliminated by azeotropic distillation of the water-benzene mixture, 40 ml of dimethylsulfoxide were added and all of the water and benzene was distilled off.

At a temperature of 50° C., 27.5 g (0.2 mol) of 2-chloro-benzonitrile were introduced and the temperature was increased to 75°±5° C. for 5 hours. The mixture was extracted with 250 ml of toluene and the organic phase was washed with water in order to eliminate the sodium chloride after which the solvent was evaporated off under vacuum.

In this way, 47.2 g of 2-(4'-chloro-phenylthio)-benzontrile were obtained, corresponding to a yield of 96%.

EXAMPLE 3

Preparation of 2-(4'-chloro-phenylthio)-benzonitrile

Into a 2 liter-reactor were introdced 300 g of methanol and, under nitrogen atmosphere, 85.05 g (1.57 mol) of sodium methylate. After this, 120 g of methanol were distilled off and the reaction medium was cooled to 30° C. whereupon 216.75 g (1.49 mol) of 4-chloro-thiophenol were added in one operation.

The mixture was refluxed for 30 minutes and the temperature was allowed to decrease to 70° C.

A solution of 200.25 g (1.45 mol) of 2-chloro-benzonitrile in 450 g of toluene was then progressively added, followed by 150 g of N,N-dimethylformamide.

After this, 530 g of the azeotrope methanol-toluene mixture were distilled off followed by 95 g of toluene.

The reaction medium was refluxed for 1.5 hour, the temperature was allowed to decrease to 60° C. and 500 g of toluene were added with 300 g of water.

The aqueous phase was decanted and the toluene phase was washed with a solution of 15 g of sodium hydroxide in 280 g of water, the temperature being maintained at 50°–55° C. A further 150 g of toluene was added and the reaction medium was washed twice with 300 g of water and finally with 7.5 g of 90% acetic acid in 300 ml of water. After the toluene and been evaporated off under reduced pressure, 357 g of 2-(4'-chloro-phenylthio)-benzonitrile were obtained. Yield: 97%

EXAMPLE 4

Preparation of 2-(4'-chloro-phenylthio)-benzonitrile

A quantity of 144.5 g (1 mol) of 4-chloro-thiophenol was mixed with 300 g of 2-methoxy-ethanol and 24.5 g (1.05 mol) of sodium were progressively added. As soon as the sodium had completely reacted, 137.5 g (1 mol) of 2-chloro-benzonitrile were added and the mixture was refluxed (118° C.).

The product was separated out as described in the above Examples and 207.2 g of 2-(4'-chloro-phenythio)-benzonitrile were obtained. Yield: 83.9%.

EXAMPLE 5

Preparation of 2-(4'-chloro-phenythio)-benzoic acid

Into a 3 liter-reactor fitted with a stirrer, a dropping-funnel and a condenser were introduced 1100 g of a toluene solution containing 355 g (1.44 mol) of 2-(4'-chloro-phenythio)-benzonitrile, prepared as in Example 1. The toluene was distilled off, first under atmospheric pressure, then under reduced pressure.

A 65% solution of sulphuric acid, obtained from 1255 g of 94% sulphuric acid and 560 g of water, was introduced over a period of 15 minutes. The reaction medium was heated to 125°–130° C. for 8 hours and the mixture was poured into a 5 liter-beaker. The mixture was cooled and 2 liters of water were added over a period of about 10 minutes.

The mixture was cooled to 20°±5° C. and this temperature was maintained for 30 minutes. The precipitate was then filtered out on a Buchner funnel and washed with water until the sulphate ions wwere eliminated. The solid was placed in a flask fitted with a reflux-condenser, 730 g of methanol were added and the mixture was refluxed for 1 hour. The reaction medium was cooled to 20° C. and, while stirring, this temperature was maintained for 1 hour. The precipitate was filtered out on a Buchner funnel and was washed with 180 g of methanol and dried in an oven.

In this way, 336.5 g of 2-(4'-chloro-phenylthio)-benzoic acid were obtained, melting at 240° C.

Yield: 88%.

EXAMPLE 6

Preparation of 2-(4'-chloro-phenylthio)-benzoic acid

Into a 3 liter-reactor fitted with a condenser were introduced 682.5 g of a toluene solution containing 200 g (0.815 mol) of 2-(4'-chloro-phenylthio)-benzonitrile, prepared as in one of the Examples 1 to 4, and the toluene was distilled off under atmospheric pressure. At the end of the operation of distillation, the mixture was cooled to 100° C. and 400 g of water were added. The elimination of the toluene was continued by azeotropic distillation of the water-toluene mixture.

The mixture was cooled to 70° C. and 400 ml of 2-methoxy-ethanol, 100 g of sodium hydroxide and 40 ml of water were successively added.

The mixture was refluxed for 6 hours and was then cooled to 80° C. While stirring, a mixture of 260 ml of 36% hydrochloric acid and 200 g of water was added. The precipitate which formed was filtered out while hot, washed until neutrality and dried. In this way, 2-(4'-chloro-phenylthio)-benzoic acid was obtained in a quantitative yield.

The final product only contained traces, lower than 0.5%, of 2-(4'-chloro-phenylthio)-benzamide, determined by thin layer chromatography.

EXAMPLE 7

Preparation of 2-(4'-chloro-phenylthio)-benzoic acid

In a reactor fitted with a condenser, there was refluxed for 8 hours at 130° C. a mixture of 245.7 g (1 mol) of 2-(4'-chloro-phenylthio)-benzonitrile, prepared as in one of the Examples 1 to 4, 701.5 g (5 mols) of 70% sulphuric acid and 245 ml of 90% acetic acid.

The mixture was cooled to 20°±5° C. and 3 liters of water were slowly added. The mixture was allowed to stand for 30 minutes at this temperature, and the precpitate which formed was filtered out and washed with 180 g of methanol.

In this way, 242.2 g of 2-(4'-chloro-phenylthio)-benzoic acid were obtained.

Yield: 91.5%. Melting point: 240° C.

The final product only contained a quantity lower than 1% of 2-(4'-chloro-phenylthio)-benzamide.

I claim:

1. Method of preparing 2-chloro-thioxanthone which comprises reacting an alkali metal derivative of 4-chloro-thiophenol with 2-chloro-benzonitrile in an organic solvent to form 2-(4'-chloro-phenylthio)-benzonitrile, hydrolyzing said 2-(4'-chloro-phenylthio)-benzonitrile to form 2-(4'1-chloro-phenylthio)-benzoic acid and cyclising said 2-(4'-chloro-phenylthio)-benzoic acid by dehydration to produce 2-cloro-thioxanthone.

* * * * *

UNITED STATES PATENT OFFICE
CERTIFICATE OF CORRECTION

Patent No. 4,264,773           Dated April 28, 1981

Inventor(s) Charles Pigerol, et al

It is certified that error appears in the above-identified patent and that said Letters Patent are hereby corrected as shown below:

Column 6, line 1, "2-(4'1-chloro-phenylthio)-benzoic" should read --2-(4'-chloro-phenylthio)-benzoic--

Signed and Sealed this

Fourteenth Day of July 1981

[SEAL]

Attest:

Attesting Officer

GERALD J. MOSSINGHOFF

Commissioner of Patents and Trademarks